United States Patent
Kopelman et al.

(10) Patent No.: US 7,074,039 B2
(45) Date of Patent: Jul. 11, 2006

(54) METHOD AND SYSTEM FOR ASSESSING THE OUTCOME OF AN ORTHODONTIC TREATMENT

(75) Inventors: Avi Kopelman, Ramat Chen (IL); Baruch Nissenbaum, Ramat Gan (IL); Leonid Rasovsky, Tel Aviv (IL)

(73) Assignee: Cadent Ltd., OR Yehuda (IL)

( * ) Notice: Subject to any disclaimer, the term of this patent is extended or adjusted under 35 U.S.C. 154(b) by 462 days.

(21) Appl. No.: 10/426,975

(22) Filed: May 1, 2003

(65) Prior Publication Data

US 2003/0215764 A1    Nov. 20, 2003

(51) Int. Cl.
    *A61C 3/00*    (2006.01)

(52) U.S. Cl. .......................... 433/24; 433/213
(58) Field of Classification Search .................. 433/24, 433/213, 214
    See application file for complete search history.

(56) References Cited

FOREIGN PATENT DOCUMENTS

| WO | WO 99/34747 | 7/1999 |
|---|---|---|
| WO | 01/80761 A2 | 11/2001 |

*Primary Examiner*—Cary E. O'Connor
*Assistant Examiner*—Candice C. Stokes
(74) *Attorney, Agent, or Firm*—Nath & Associates PLLC; Gregory B. Kang; Derek Richmond

(57) ABSTRACT

A virtual orthodontic treatment method and a system thereof, the method comprising the following: providing a virtual diagnostic setup model of teeth of at least one jaw of an individual, associating each teeth in said model with its corresponding virtual orthodontic appliance to obtain a first composite model and repositioning teeth into an initial treatment state according to pre-defined appliances-dependent rules. In the initial treatment state, selecting one or more teeth and reassociating the teeth with their corresponding virtual orthodontic appliance by changing the position of the appliance corresponding to the selected tooth thereby causing repositioning of the teeth according to the appliance-dependence rules. An altered treatment state is obtained, yielding a better grade, according to one or more systems for grading an orthodontic model, as compared to the grade of the initial treatment state.

78 Claims, 11 Drawing Sheets

METHOD AND SYSTEM FOR ASSESSING THE OUTCOME OF AN ORTHODONTIC TREATMENT

FIELD OF THE INVENTION

The present invention is generally in the field of orthodontics. More specifically, the present invention relates to a computerized method and system for virtual orthodontic treatment which may assist an orthodontist in designing an orthodontic treatment plan.

BACKGROUND OF THE INVENTION

Orthodontic therapy has the object of aligning and repositioning teeth for both functional and aesthetic purposes. This is achieved by the use of a variety of orthodontic appliances including, brackets, wires (arch wires), coil springs and elastics. In combination, these appliances are fixed to teeth in such manner that orthodontic forces and moments cause the teeth to move in the desired direction.

There are currently acceptable guidelines in orthodontics, which define the optimal dental and skeletal relations which should be the goal of the orthodontic treatment. A summary of such guidelines can be found in *Straight Wire, the Concept and Appliances*, by Laurence F Andrews, L.A. Well, Co., San Diego, Calif., USA, 1989. These guidelines are based on both functional and aesthetic considerations.

A common problem in the orthodontic field is the lack of space in the dental arch called dental crowding. In this clinical situation the orthodontist should decide if his orthodontic treatment plan will include the solution of tooth extractions (which is an irreversible procedure), how teeth should be moved against anchorage units during the treatment protocol and accordingly what orthodontic appliances should be chosen and how to apply them on the teeth to achieve a desired outcome. The procedure of assessing the best treatment plan by the orthodontist is typically based on patient clinical measurements, plaster cast and radiographic analysis, the orthodontist's personal "look and feel", and his prior experience and skills. In some cases it also required to prepare wax-based diagnostic setup model which exhibits the possible end result of the orthodontic case. This approach is time consuming and also does not permit to easily visualize the outcome of several treatment options at the same time.

There is accordingly a need in the art to provide the orthodontist with a tool which enables him to design the treatment procedure—which will yield an optimal outcome, and to analyze possible outcome of different treatment methods.

PCT Application WO 99/34747 describes a method for virtual orthodontic treatment, which utilizes a virtual set of orthodontic components, in a virtual computerized environment. A set of rules, which are mainly geometric rules, are applied to move the teeth by the use of standard and non standard virtual orthodontic components.

SUMMARY OF THE INVENTION

The present invention provides a method and system for virtual orthodontic treatment. The virtual orthodontic treatment may be used by an orthodontist to evaluate possible outcomes of the orthodontic treatment. The present invention also provides, by one preferred embodiment, a computerized method and system for designing the real life orthodontic treatment scheme for a specific individual.

The following are some terms which will be used herein and their meanings:

The term "virtual orthodontic treatment" will be used to denote a virtual set of operations that is carried out on a virtual diagnostic setup model using a virtual set of orthodontic appliances within the virtual computer environment. In the virtual orthodontic treatment teeth are repositioned according to rules that are dictated by the virtual orthodontic appliances. For example, where the orthodontic appliances include a straight arch wire set comprising a straight arch wire and brackets attached to the teeth with the arch wire received in a slot within the bracket, the rules may dictate that the outcome of the treatment should be that all grooves of all brackets be in a plane defined by the arch wire with the teeth aligned along an arch defined by said arch wire.

The term "virtual diagnostic setup model" refers to a virtual teeth model with the teeth separated such that each tooth can be repositioned.

The term "reposition" will be used to denote, collectively, a change in the position of a tooth in the anteroposterior direction, in a vertical direction from a more attracted to a more extracted state or vice versa, an angular change in the buccullingual inclination, an angular axial change in orientation of a tooth, and in general any change in position and/or orientation of a tooth.

The term "associated" or "association" will be used to denote the virtual physical relationship between the teeth of the virtual diagnostic setup model and the virtual orthodontic appliances such that the teeth will be repositioned according to appliances-dependent rules, similar to the manner in which such appliances cause repositioning of teeth in real life orthodontic treatment. For example, the association of brackets with teeth involve attachment of brackets to the teeth's crown, or fixing an orthodontic band with integral bracket over a tooth. Association of arch wire involves snapping of the arch wire into a groove defined on the external face of the bracket.

The term "reassociated" or "reassociation" will be used to denote repetition of the act of association, by changing the position of the virtual orthodontic appliances to a different location on the tooth and thus causing repositioning of teeth according to appliances-dependent rules. Thus, reassociation includes detaching appliances from teeth, repositioning at least one appliance on at least one tooth, and reattaching appliance with the tooth for association of appliances with teeth. Some other terms are used herein, which generally have a meaning similar to that ascribed to these terms in a real life orthodontic treatment, or have meaning that become clear from the context in which they are used. It should be understood that use of physical terms such as "repositioning", "extraction", etc., refers to such manipulations performed within the virtual computer environment, unless it otherwise becomes clear from the context.

The present invention is based on a novel concept for virtual orthodontic treatment. In accordance with the invention, a virtual set of orthodontic appliances is associated with teeth of a virtual diagnostic setup model to obtain a first composite model, and the teeth are permitted to reposition into an initial treatment state according to pre-defined appliances-dependent rules. Typical rules in the case of use of brackets and a straight arch wire set that comprise brackets and a straight arch wire include alignment of all horizontal slots on the face of the bracket that receive the arch wire on a plane defined by the wire and alignment of the teeth along the arch defined by the arch wire. Upon achieving said initial treatment state, one or more teeth are virtually reassociated with the appliances and repositioned such so as to obtain an improved treatment state that yields a better grade, according to one or more systems for grading orthodontic models, as compared to the grade of said initial treatment state. Then the orthodontic appliances may be reassociated with the teeth in a manner as to match the new position of the teeth. The reassociating procedure is repeated a plurality of times, with different types of teeth repositioning, to achieve the highest possible grade.

For the purpose of designing an orthodontic treatment plan, following repositioning and reassociation of the orthodontic appliances with the teeth, the teeth are reverted back to their initial position in the virtual diagnostic setup model with the orthodontic appliances remaining attached thereon. The association of the orthodontic appliances set with the teeth in the resulting composite model will thus be different than that in the first composite model. This resulting composite model may be thus used by an orthodont to design the manner of association of the orthodontic appliances with teeth within the framework of the real life orthodontic treatment. Such association will give rise to result in the real life treatment similar to those of the virtual orthodontic treatment carried out in accordance with the invention.

The invention thus provides a virtual orthodontic treatment method, that comprises:

providing a virtual diagnostic setup model of teeth of at least one jaw of an individual, associating virtual orthodontic appliances with teeth in said model to obtain a first composite model and repositioning teeth into an initial treatment state according to pre-defined appliances-dependent rules;

in said initial treatment state, selecting one or more teeth and reassociating teeth with their corresponding virtual orthodontic appliances by changing the position of the appliance corresponding to the selected tooth thereby causing repositioning of the teeth according to the appliance-dependence rules to obtain an altered treatment state, yielding a better grade, according to one or more systems for grading an orthodontic model, as compared to the grade of said initial treatment state.

The present invention also provides a system for virtual orthodontic treatment, that comprises (i) a digital interface for receiving digital data representative of a virtual diagnostic setup model of teeth;

(ii) a processor including a software for associating virtual orthodontic appliances with teeth in said model to obtain a first composite model, repositioning teeth into an initial treatment state according to pre-defined appliances-dependent rules, and for in said initial treatment state, selecting teeth and virtually resassociating said orthodontic appliances with teeth, by repositioning appliances on at least the selected teeth to obtain an altered treatment state, thereby obtaining a second composite virtual model yielding a better grade, according to one or more systems for grading an orthodontic model, as compared to the grade of said initial treatment position; and (iii) a user interface comprising at least a display for displaying results of the virtual orthodontic treatment.

Also provided by the present invention in accordance with a preferred embodiment, is a method for designing a real life orthodontic treatment comprising:

(a) providing a virtual diagnostic setup model of an initial state of teeth of at least one jaw of an individual, associating virtual orthodontic appliances with teeth in said model in a first association arrangement to obtain a first composite virtual model;

(b) repositioning teeth according to pre-defined appliances-dependent rules, to obtain an initial treatment state with a second association arrangement of said teeth and said appliances;

(c) in said initial treatment state selecting one or more teeth and virtually detaching between at least the selected teeth and said orthodontic appliances, repositioning said appliances on the teeth and reattaching appliances with teeth thereby altering treatment state, yielding a better grade, according to one or more systems for grading an orthodontic model, as compared to the grade of said initial treatment state, and obtaining a second composite virtual model; and (d) permitting the teeth to revert back from their state in said second composite virtual model into said initial state with said orthodontic appliance remaining associated with the teeth in a manner as in said second composite virtual model to obtain a treatment-design virtual model with orthodontic appliances associated with the teeth in a manner of association to be applied in a real life orthodontic treatment.

Still further provided in accordance with this preferred embodiment is a system for designing a real life orthodontic treatment, comprising:

(i) a digital interface for inputting a virtual diagnostic setup model of an initial state of teeth of an individual;

(ii) a user interface comprising at least an output for outputting results of virtual orthodontic treatment and information on design of real life orthodontic treatment;

(iii) a processor including a software running thereon for associating virtual orthodontic appliances with teeth in said model in a first association arrangement to obtain a first composite virtual model, repositioning teeth according to pre-defined appliances-dependent rules, to obtain an initial treatment state with a second association arrangement of said teeth and said appliances, in said initial treatment state selecting one or more teeth, virtually reassociating said orthodontic appliances from teeth by repositioning appliances on at least selected teeth to obtain an altered treatment state, yielding a better grade, according to one or more systems for grading an orthodontic model, as compared to the grade of said initial treatment state, thereby obtaining a second composite virtual model, permitting the teeth to revert back from their state in said second composite virtual model into said initial state with said orthodontic appliance remaining associated with the teeth in a manner as in said second composite virtual model to obtain treatment-design virtual model with orthodontic appliances associated with the teeth in a manner of association to be applied in a real life orthodontic treatment, and outputting data representative of said treatment-design virtual model in a manner suitable for use in the design of the real life orthodontic treatment.

The grading system, according to one embodiment, is based on measuring one or more of the following parameters: alignment, marginal ridges, buccollingual inclination, overjet, occlusal relationship, occlusal contacts and interproximal contacts. Each of these parameters has a defined standard and the grading may be based on the extent of deviation of the measured parameter from said standard.

Alignment is usually a fundamental objective of an orthodontic treatment plan. In the maxillary and mandibular interior regions, proper alignment is typically characterized by coordination of alignment of the incisor edges and the lingual incisor surfaces of the maxillary incisors and canines, and the incisor edges and labial incisor surfaces of the mandibular incisors and canines. In the mandibular posterior region, for proper alignment, the mesiobuccal and distobuccal cusps of the molars and premolars should be in the same mesiodistal alignment. In the maxillary arch, for proper alignment, the central grooves should all be in the same plane or alignment. Preferably, the deviation should be within 0.5 mm of proper alignment.

Marginal ridges are used to assess proper vertical positioning of the posterior teeth. In both maxillary and mandibular arches, marginal ridges of adjacent posterior teeth should be the same level, or preferably within 0.5 mm of the same level.

Buccolingual inclination is used to assess the buccolingual angulation of the posterior teeth. The buccolingual inclination of the maxillary and mandibular posterior teeth is assessed by measuring the distance between the lingual cusps and the straight line that connects buccal cusps of contra lateral teeth. Such a vertical distance preferably below 1 mm is typically permitted.

Occlusal relationship is used to assess the relative anteroposterior position of the maxillary and mandibular posterior teeth. For a proper relationship, the buccal cusps of the maxillary molars, premolars and canines should preferably align within 1 mm of the interproximal embrasures of the mandibular posterior teeth. The mesiobuccal cusps of the maxillary first molar should prefereably align within 1 mm of the buccal groove of the mandibular first molar.

Occlusal contacts is a measure that assesses the adequacy of the posterior occlusion. For proper occlusal contacts, the buccal cusps of the mandibular premolars and molars and the lingual cusps of the maxillary premolars and molars should be contacting the occlusal surfaces of the opposing teeth.

Overjet is a measure used to assess the relative transverse relationships of the posterior teeth and the anteroposterior relationship of the anterior teeth, typically, in the posterior region, the mandibular buccal cusps and maxillary lingual cusps are used to determine proper position within the fossae of the opposing arch. In the anterior region, the mandibular incisor edges should be in contact with the lingual surfaces of the maxillary anterior teeth. In case of a proper overjet, the buccal cusps of the mandibular molars and premolars will contact in the center of the occlusal surfaces, buccolingually, of the maxillary premolars and molars. In the anterior region, the mandibular canines and incisors will contact the lingual surfaces of the maxillary canines and incisors.

Interproximal contacts is used to determine if all spaces within the dental arch have been closed.

For grading, the virtual teeth mode, whether in said initial treatment state or in the altered treatment state, may be graded by one of these parameters by determining the extent of deviation from established or conventional standards. It should, however, be appreciated that the invention is not limited to the use of the above parameters for grading of the virtual teeth model and also not to any specific standard applied for grading. On the contrary, any parameter or any standard acceptable or that will become acceptable may be employed within the framework of the present invention, for grading of the virtual teeth model.

The grading system that can be used may be that established by the American Board of Orthodontics (ABO) for grading dental cusps for Phase III clinical examination for candidates requested to become members of ABO (John S. Casko, et al., The American Board of Orthodontics, Grading System for Dental Casts and Panoramic Rodeographs, November 1998).

The virtual set of orthodontic appliances used in the method and system of the invention, typically comprise brackets and arch wires. In accordance with a preferred embodiment of the invention, the orthodontic appliances comprise straight-wire appliances. In addition to wires and brackets, the virtual set of orthodontic appliances may also include a variety of other appliances such hooks, springs, expansion screws, wire locks such as Gurin locks, hooks, orthodontic bands, orthodontic elastics such as rubber bands or springs, etc. In accordance with some embodiments of the invention, rather than a single straight wire, virtual loops, bands or twists or bands may be introduced into the wire.

In the case of the use of a virtual set of straight wire appliances, the brackets are typically fixed initially at the center of the crown of the teeth and the teeth are then permitted to reposition so that the slots of all brackets align in the plane defined by the arch wire and the teeth are aligned along an arch defined by said arch wire.

In said initial treatment stage, appliances may be detached from their associated teeth and then repositioned in a manner to give a higher grade, following which the bracket and/or other orthodontic appliances may be reattached to the tooth. This step may be repeated a plurality of times so as to yield an optimal result yielding the best grade.

In accordance with some embodiments of the invention, the user may be permitted to select a set of orthodontic appliances that will be associated with the teeth. In other embodiments of the invention, this is automatic.

Similarly as in real life orthodontic treatment, also in the virtual treatment in accordance with the invention, additional virtual orthodontic interventions may be carried out. These additional interventions may include, for example, a tooth extraction or tooth stripping. Here again, in some embodiments of the invention, the need for an additional orthodontic intervention is automatically established and the type of additional orthodontic intervention is automatically selected. In other embodiments of the invention, the need and nature of initial orthodontic intervention is defined by the user.

Such additional orthodontic interventions may, for example, be a tooth extraction or interproximal stripping of a tooth.

In some embodiments the grading system used is automatically selected by the system. In other embodiments, the user may be permitted to manually select a certain grading system. A preferred grading system for grading the above parameters is said ABO grading system. The grading may be automatic or may be carried manually through the user interface.

Where the virtual treatment method or system serves for a design of an orthodontic treatment, data representative of association of orthodontic appliances with the teeth to achieve orthodontic treatment targets as determined through the virtual treatment method or system is obtained. Data of such association may be output to a display or a suitable treatment guidance system.

By the method and system of the invention the orthodontist can visualize, e.g. on a screen, how the final outcome of the treatment will be when using a specific set of orthodontic appliances. In addition, the orthodontist may also assess the effect of a variety of additional manipulations that in real-life orthodontic treatment are irreversible, such as extraction and/or stripping of one or more teeth. This procedure may also be automatic according to some embodiments of the invention. Based on the outcome of the procedure, which, as aforesaid may be visualized on a screen, the orthodontist may decide whether to use the selected orthodontic appliances and the additional intervention for the treatment of the specific individual or change one or more of the procedure parameters such as the type of wire, type of brackets, type of tooth to be extracted, etc., and test the outcome with the newly selected parameters. Eventually, the orthodontist will obtain, in accordance with the invention, a three-dimensional digital model which yields a desired outcome; and a set of virtual appliances, their positioning and other manipulations which yielded this desired result, that can then be applied in the real life orthodontic treatment plan.

The virtual diagnostic setup model of the teeth may be prepared on the basis of a teeth impression. Teeth impressions are used in the art to prepare plaster models, and the digital three-dimensional model will typically have an overall representation resembling that of a plaster model. The preparation of plaster models and the like are known in the art of orthodontry. Methods for obtaining a three-dimensional digital model of teeth of an individual are generally known and one such method is described in U.S. Pat. No. 6,099,314 that is incorporated herein by reference.

The virtual diagnostic setup model is inputted to the system as a digital representation of data that can be processed by a computer, and when presented, for example, on the computer's screen, resembles the three-dimensional structure of a real life physical model. A virtual diagnostic setup model of teeth includes at least a representation of the external contours of the teeth and the separation if teeth from their adjacent teeth, but preferably also includes a representation of portions of the gums. The virtual setup model may be visualized on a screen in a manner resembling a plaster setup model used in orthodontry.

The invention will now be further illustrated by the following embodiments with occasional reference to the annexed drawings.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
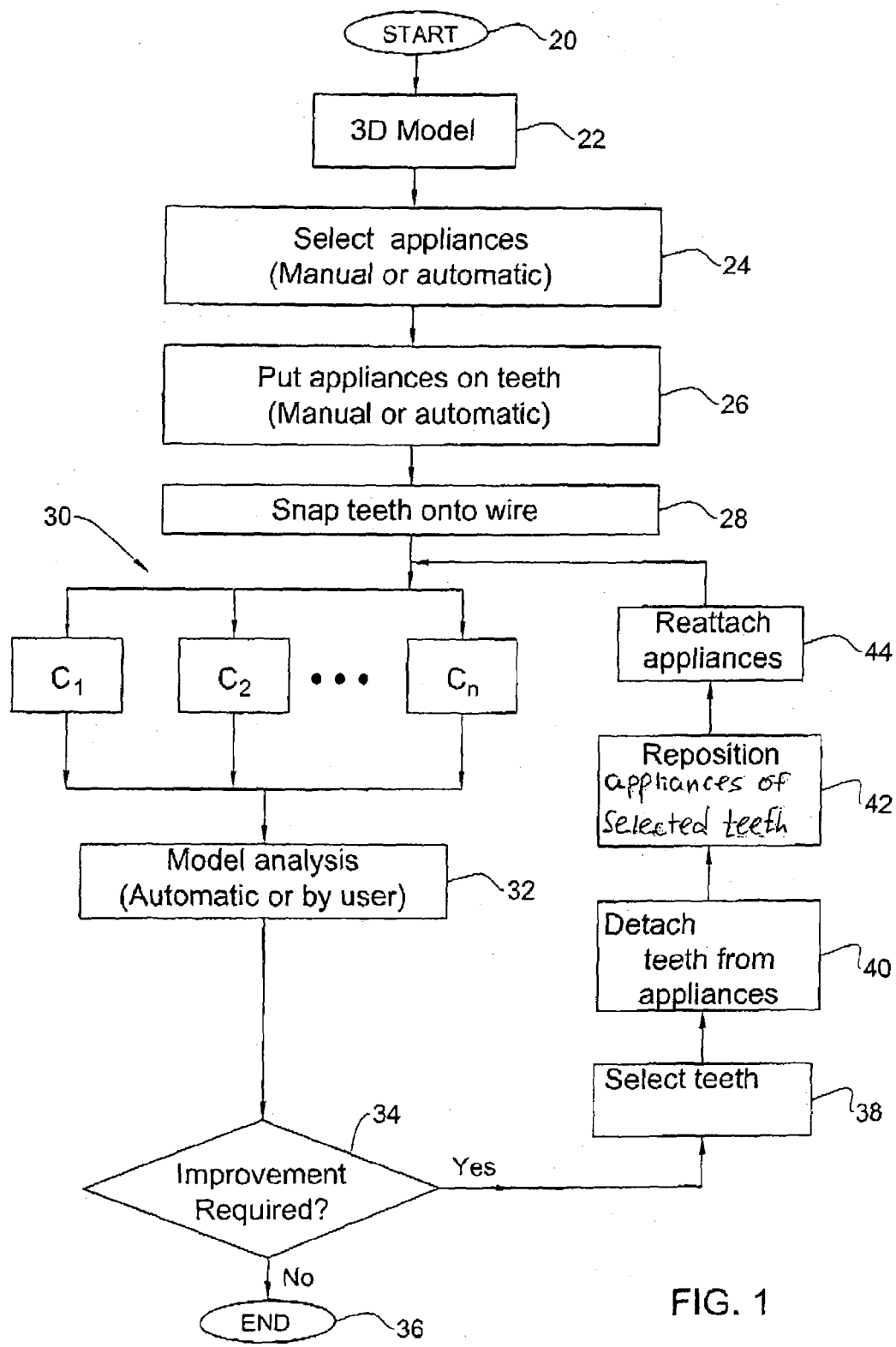
FIG. 1 shows an overall flow chart of a virtual orthodontic treatment in accordance with an embodiment of the invention.

Reference is first being made to FIG. 1 that shows a general flow chart of an embodiment of the virtual treatment method in accordance with the invention. Upon initiation 20, a virtual diagnostic setup model is inputted. This model may be obtained by a number of different ways. The basis is a virtual teeth model obtained through a variety of teeth scanning or direct teeth imaging techniques or through scanning or otherwise capturing a negative teeth impression or a positive teeth model. An example of a method for obtaining three-dimensional digital model of teeth is disclosed in U.S. Pat. No. 6,099,314. From such a model a virtual setup model may be obtained through an automatic or manual procedure in which the setup model the teeth are separated from one another in a manner that permits separate manipulation of the position of each of the teeth.

At the next step 24 a set of orthodontic appliances is selected for subsequent association with the teeth. As will be appreciated, the invention is not limited to a specific set of orthodontic appliances and the general principle described herein applies to any selected set. However, in accordance with a preferred embodiment of the invention, the set of orthodontic appliances which is to be used is a straight wire set that comprises a straight wire and brackets. As known, each bracket has a horizontal slot for receiving the wire. In addition, similarly as in real life orthodontic treatment, other orthodontic appliances such as hooks, elastic components, and others may be included in the set. The selection of the set may be automatic by the system or may be manual. For selection of a set of orthodontic appliances, different options may be presented to the user, for example, sets of different manufacturers, and the orthodont may then choose the one most familiar to him or the set which he prefers to use. Alternatively, rather than selecting a complete set, optionally the user may select individual components that together will comprise the set.

At a next step 26 the appliances are attached to or made to associate with the teeth. In one embodiment of the invention this is an automatic operation. In such an embodiment, after selection of the set for orthodontic appliances, the brackets are automatically attached to teeth. In such an automatic attachment, the brackets are typically attached to the center point of the teeth crown (namely at the center of the exposed surface of the teeth). In accordance with another embodiment the user may be permitted to select the position of all or of only some of the brackets.

Once all brackets have been selected, a wire, typically a straight wire as pointed out above, is added, and the first sequence of orthodontic treatment follows. In this first sequence, teeth are repositioned in a manner so that all the wire-receiving slots on the brackets snap onto the wire. This causes all slots to align in the plane defined by the wire and the teeth to align in an overall arch is also defined by the wire. This step may be carried out, for example, in a manner as described in PCT Publication WO 99/34747. Thereby, a first treatment state of the virtual model is obtained. A more detailed description of the step appears further below.

In a next step 30, this initial treatment state is analyzed and graded by a variety of criteria C1, C2, . . . CN. These grading criteria include, in accordance with a preferred embodiment of the invention, the following: alignment, marginal ridges, buccolingual inclination, overjet, occlusal relationship, occlusal contact and interproximal contacts. Reference is made to the explanation above of these criteria. The grading, as pointed out above, is based on the deviation of the teeth arrangement from a standard or ideal arrangement, in accordance with one or more of established standards. An example of a standard which may be applied is that set by the American Board of Orthdontics, referenced above. It should, however, be noted that in some embodiments only part of the above criteria or at times even one, e.g. only the criteria of alignment, may be used to grade the teeth arrangement. In a typical embodiment of the invention, the grading is carried out automatically, although optionally, the grading may be manually done by the user.

Following the grading according to one or more of the above criteria, at a next step 32 an overall model analysis is carried out. In this analysis the different grading scores are combined, which combination may be a simple combination, may be a weighted combination (ascribing a different way to a different criteria) or any other acceptable analysis of the system. Here again, the overall model analysis is typically automatic, although it is possible also to permit the user to do it manually.

Following this overall analysis, at a distant point 34 an assessment is made whether the model meets orthodontic standards or whether an improvement is required. If no improvement is required, the virtual treatment ends 36. If a decision is made and an improvement is required, which decision may be automatic or may be a decision made by the user, a next step 38 teeth for repositioning are selected, then at 40 the orthodontic appliances are virtually detaching from at least the selected teeth, the detached appliances are then repositioned at 42, to effect repositioning of the teeth. For example, where a bracket is repositioned to a different lateral portion of the tooth, it effects axial rotation of the tooth. Where, by another example the bracket is repositioned to a different vertical position of the tooth crown, it effects extraction or retraction of the tooth. Where, by a further example, the attachment of the bracket to the wire is the different anteoposterior point on the wire, it effects the tooth to moved in the anterior or posterior direction.

It should be noted that optionally in steps 40 and 42, orthodontic appliances are at least temporary removed or hidden for easier visualization of the manipulation outcome.

Then, at 44, the detached orthodontic appliances are reattached to the teeth and a resulting altered treatment state is obtained. The appliances repositioning may be done using an optimization algorithm employing one of many optimization or goal-seeking algorithms where the variable set is the set of appliances positions and the goal is best grade. Possible algorithms include Deepest descent, Newton-Raphson method and others. In addition, the goal may also include additional restrictions such as having minimal angle between teeth to avoid results that may give a goal grade but are less aesthetically appealing.

The resulting altered treatment state so obtained is analyzed and graded in the same manner as described above.

Typically in the orthodontic treatment, each tooth is assembled with its corresponding bracket such that the base point of the bracket falls initially on the facial axis point of the tooth, as typically done in orthodontry. The assembled teeth may then translocate along the wire's curve according to the following criteria:

(i) The two central incisors are translocated along the wire curve (along the curve falling on the Andrews plane) until they are brought into at least one point of contact, preferably such that their contact point falls on the mid-platal plane.

(ii) The lateral incisors on each side of the mid-platal (the left and right lateral incisors) may be translocated towards their respective central incisors (i.e. the left and right incisors, respectively), followed by translocating the canine, premolar (first premolar, then premolar) and molar (for the first molar, then second molar and optionally then the third molar) teeth such that each flanking teeth have at least one point of contact therebetween. It should be clear that the same procedure is applied whenever a tooth is extracted or stripped, taking into consideration which tooth exactly was extracted.

The outcome of the above procedure is an arch wire set with brackets which are fixed with the respective tooth, the teeth being optimally arranged according to orthodontic criteria. At times, movement of the first molar teeth by the system of the invention may result in a distilization of the mandibular molar teeth in an amount greater than that allowed in a real life treatment according to real life treatment considerations. Accordingly, after translocation of teeth as described above, the system verifies whether the mandibular distilization performed would be allowed in real life considerations and if in the negative, the result displayed on the display screen, will show the user that the procedure performed would not be feasible in the real life orthodontic treatment. The user will then know that the orthodontic treatment plan he selected should be changed, e.g. by selecting a different wire, different brackets, performing other, if any manipulations on the teeth, etc.

The resulting arrangement of the teeth may further be processed by applying a vertical repositioning of the teeth, and if necessary, move in a manner similar to that in step (ii) above. The result obtained for one arch, i.e. the maxillary arch or the mandibular arch, is then used for determination of the inter arch relationship.

The algorithm employed may also use some optimization criteria for obtaining the initial treatment stage. For example, the mandibular arch may be first aligned with the mandibular jaw by their central point (an average distance between the central incisors) to fall onto the mid palatal plane. The maxillary arch fixed onto the maxillary jaw may then be vertically aligned onto the mandibular jaw in the manner as described in PCT Publication No. WO 98/52493. The alignment between the two jaws may be according to a fixed mandibular jaw or alternatively according to a fixed maxillary jaw.

The following description refers to alignment of the maxilla according to the fixed mandibular jaw. However, it should be understood that the same steps apply in flow diagram, for alignment of the mandible according to the fixed maxilla jaw (*muatis mutandis*).

For determining the inter arch relationship, first the parameters of the mandibular jaw are provided, with which the mandibular arch is aligned by determining their center antheroposterior point (lower center point A-P56). Then occlusion of the mandibular first molar with the maxillary first molar is dictated by the features of Class (I) type of occlusion. If necessary, i.e. when the outcome obtained and displayed on the display screen is not the desired outcome or when the user decides it is required to change the Class type, he may change the class by which the mandibular first molar and the maxillary first molar interlock until reaching the desired outcome.

At times, the horizontal alignment performed will result in a mandibular distilization which is greater than that acceptable in real life orthodontic treatment. As a result, the procedure according to the invention may be carried out while each arch is positioned onto their respective jaw by defining their center antheroposterior point, the steps of interlocking the molar teeth according to standard orthodontic guidelines is not performed.

Figure 3:
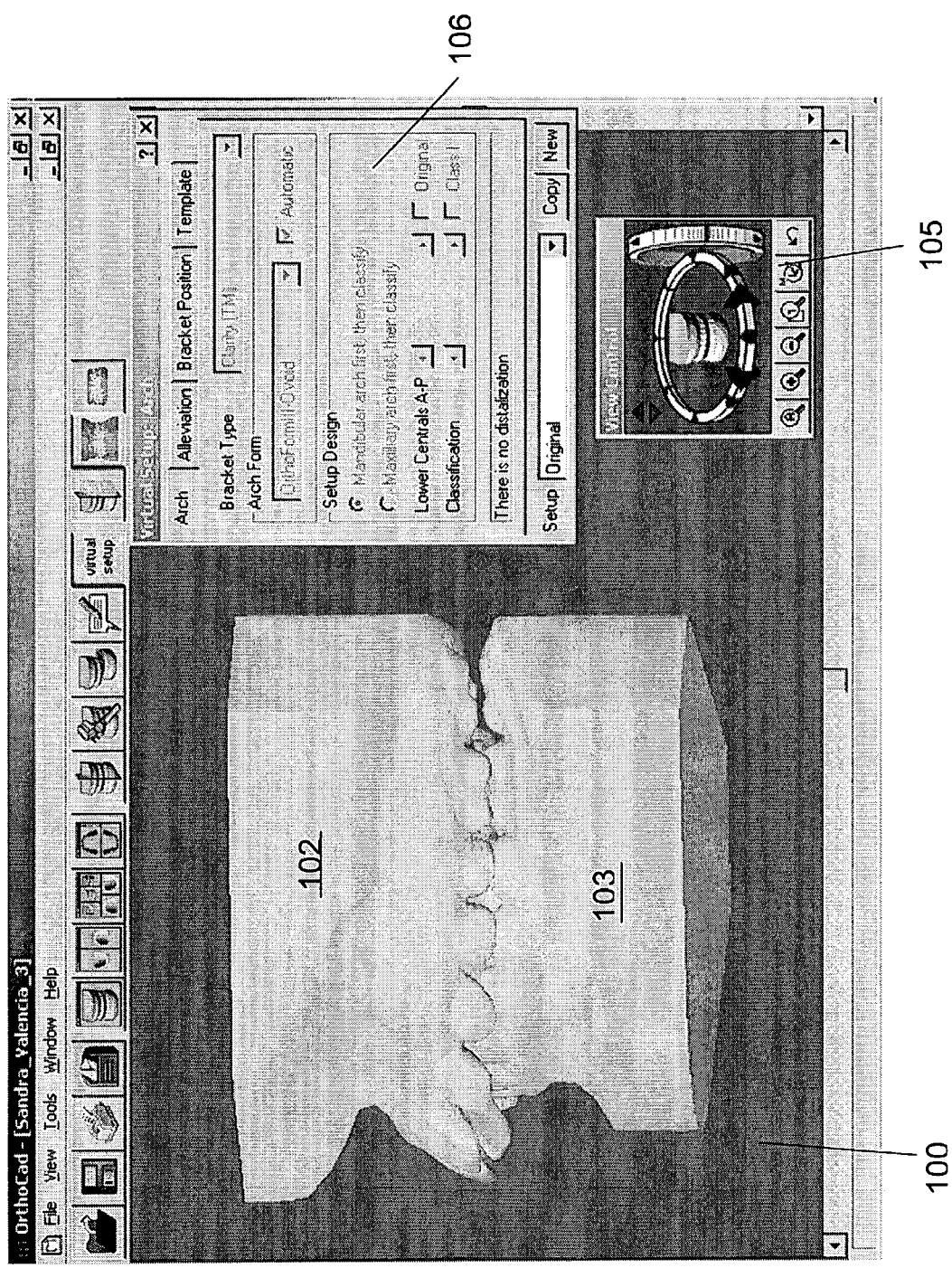
FIGS. 3 and 4 are screen displays showing, respectively, a side and a front view of a jaw of an individual before applying any virtual orthodontic procedure in accordance with the present invention.

The definition of the different classes which can be selected by the user in a manner as shown herein in FIG. 3, which shows an example of a screen display showing a virtual model 100 with an upper jaw 102 and a lower jaw 103. Shown in this view is also a view control window 105 which permits control of position of orientation as well as view angles in a manner as described in PCT Application, Publication No. WO 98/53428. The treatment parameters may be controlled through user interface window 106.

Figure 4:
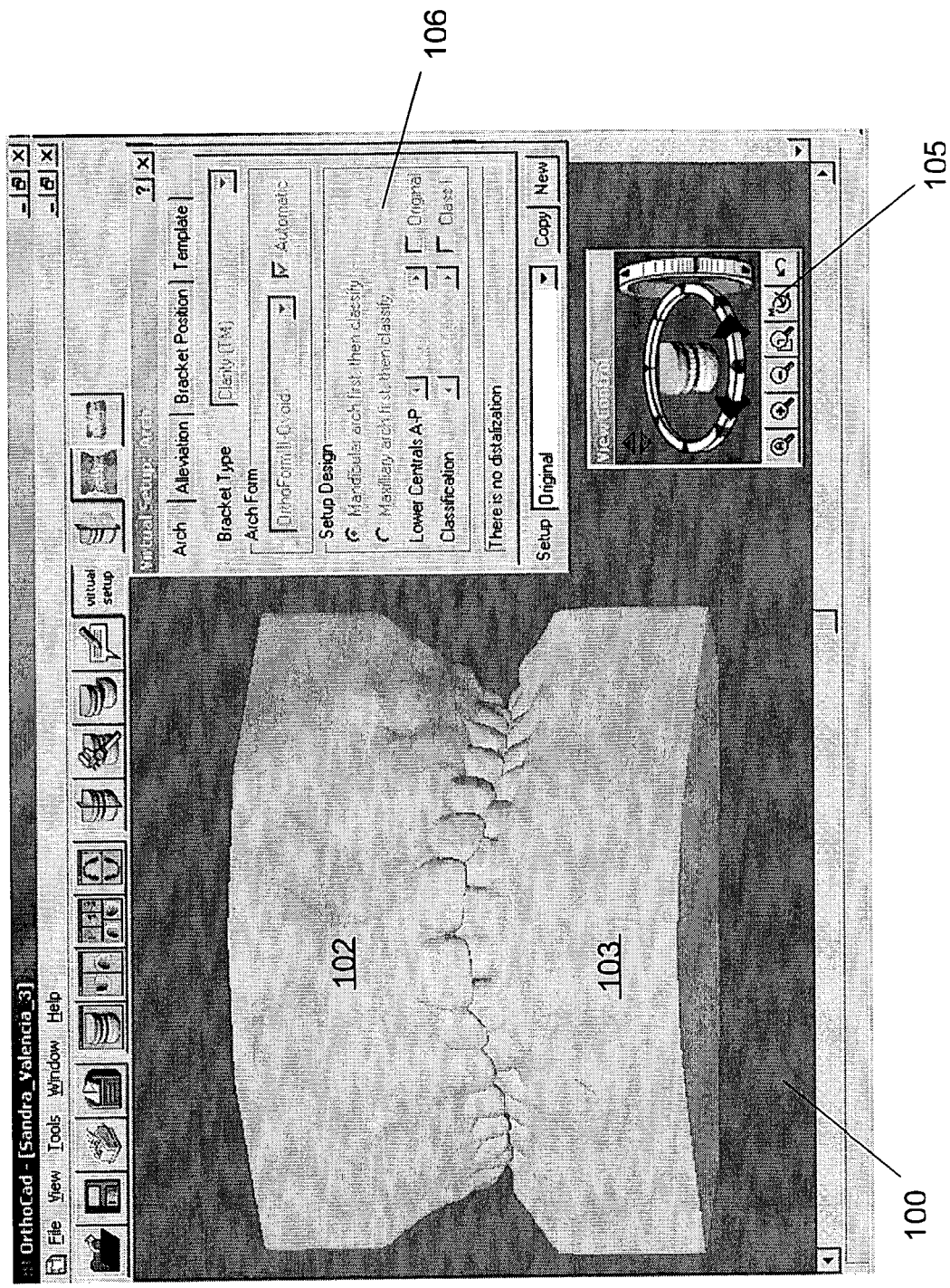

A front view of the same jaw is seen in FIG. 4.

Figure 5:
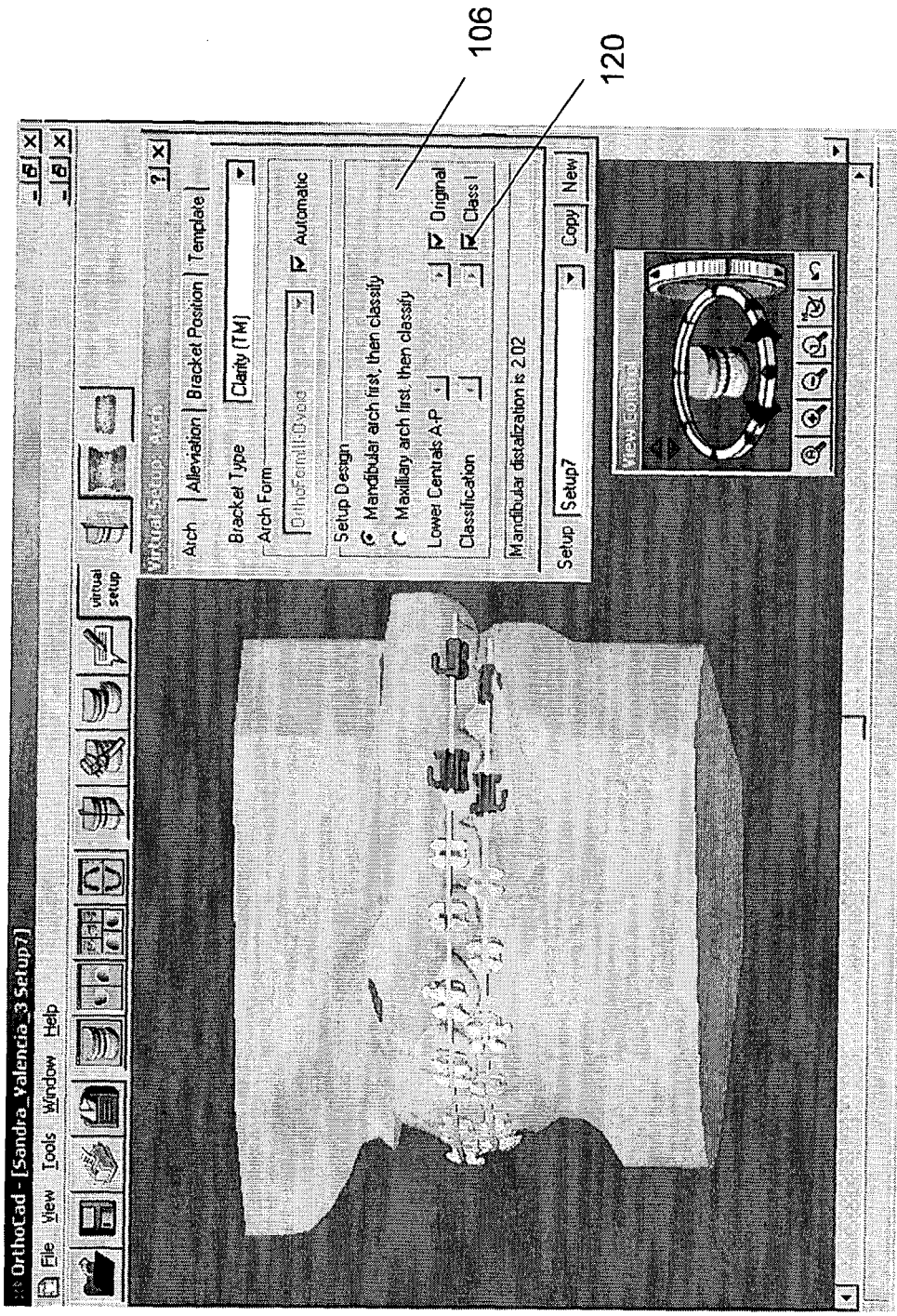
FIGS. 5 and 6 are screen displays showing the same jaws as in FIGS. 4 and 5 after performing a virtual orthodontic treatment in accordance with the invention in respective side and front view.
Figure 6:
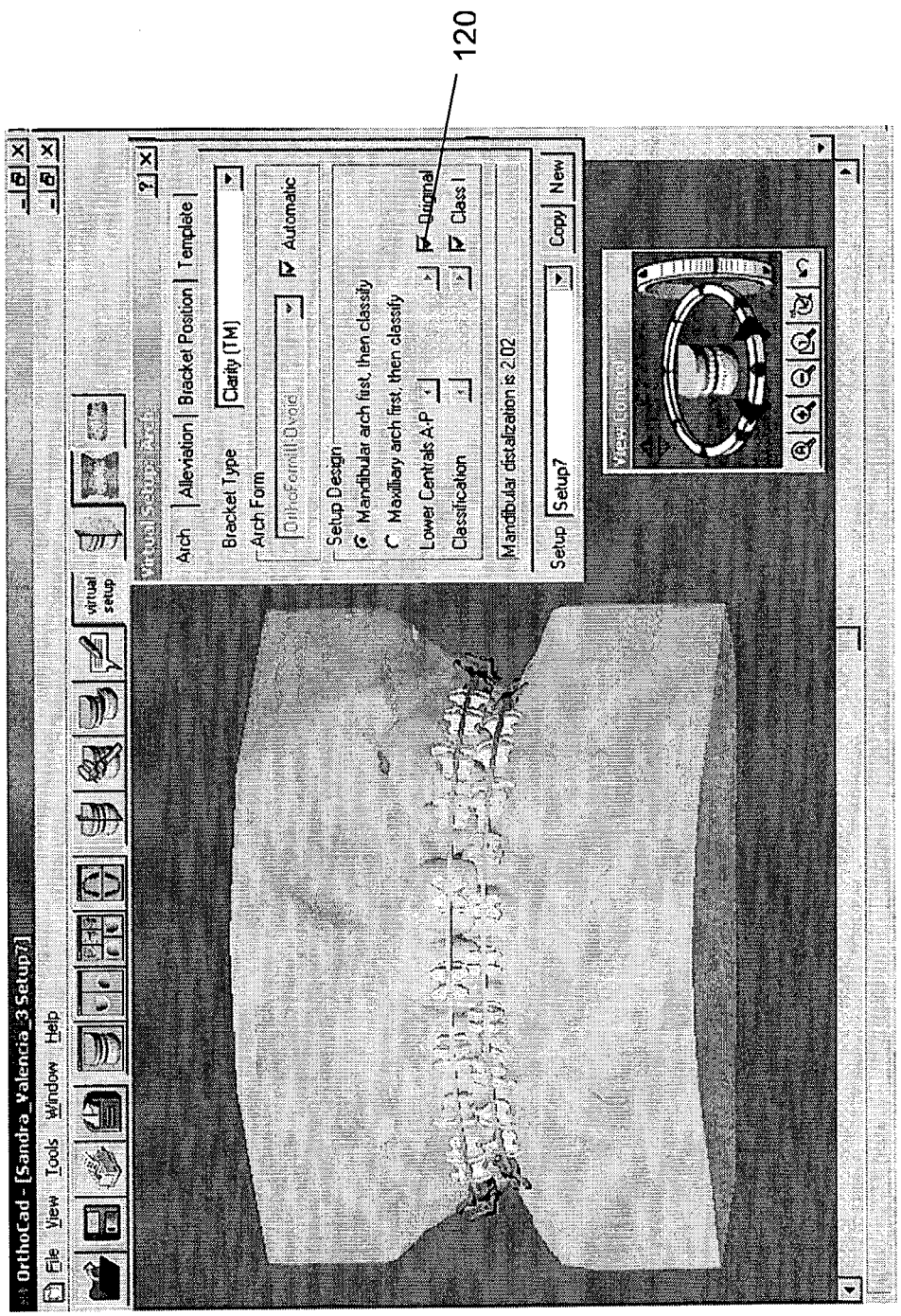

FIGS. 3 and 4 also show a virtual diagnostic setup model of an individual's jaws, in its original, untreated form. Once an orthodontic treatment is executed, a second three dimensional digital model is obtained. The second three dimensional digital model includes the jaw carrying teeth assembled with brackets and a wire. The teeth in the second model are arranged in an optimal dental and skeletal arrangement as obtained by the system of the invention. The teeth are automatically associated with brackets, the later set on a wire. The outcome of virtual treatment of the original model (shown in FIGS. 3 and 4) is seen in FIGS. 5 and 6. In this case the parameters of the system were automatically selected, including the arch wire (RothoFormIII-Ovoid), the brackets (Clarity™), and class (Class I) and yielded one optimal outcome.

There are different classes which may be applied. Class I, which is a default Class in the system and is that applied in FIGS. 5 and 6. Change in the Class may be achieved by ticking off box 120 in user interface window 106 and moving scroll bar 122 to either side.

Figure 7:
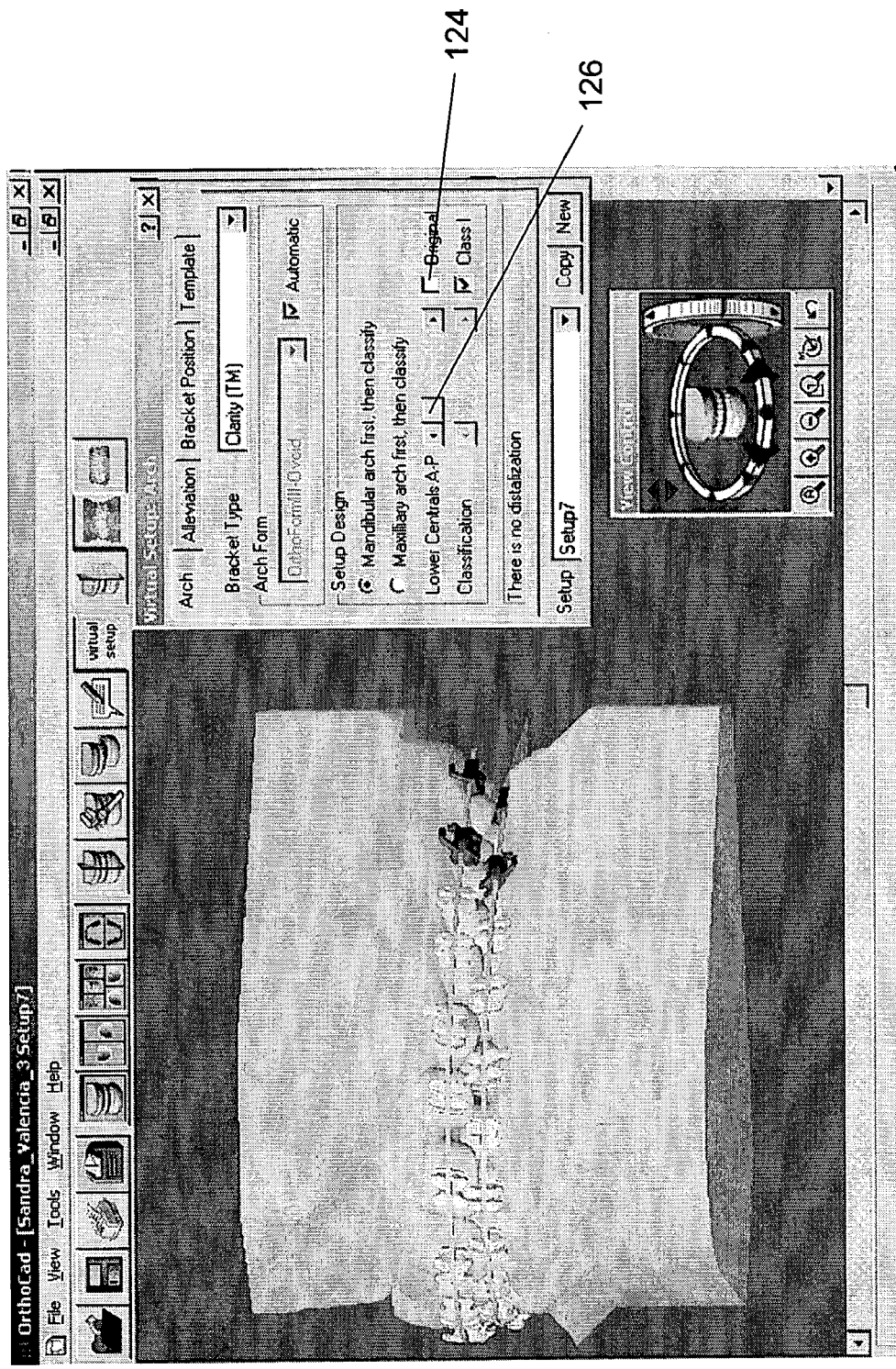
FIG. 7 shows a screen display of the same jaws as in FIGS. 4 and 5 in which the lower center A-P point selected was different than in the previous results shown in FIGS. 5–6.

Another parameter which may be selected is a lower center point, which may be automatically selected (the automatic selection is dictated by the original center point in the individual's jaw before treatment), as in FIGS. 3–6 or, it may be moved between the interior posterior direction by ticking oft box 124 and moving scroll bar 126 to either the left, as seen in FIG. 7 or the right directions.

In addition, the arch wire selection may be automatic, as in FIGS. 6 and 7, which in this case is the default arch wire known as Ortho Formll-Ovoid, but may also be manually selected within selection window 130.

Figure 8:
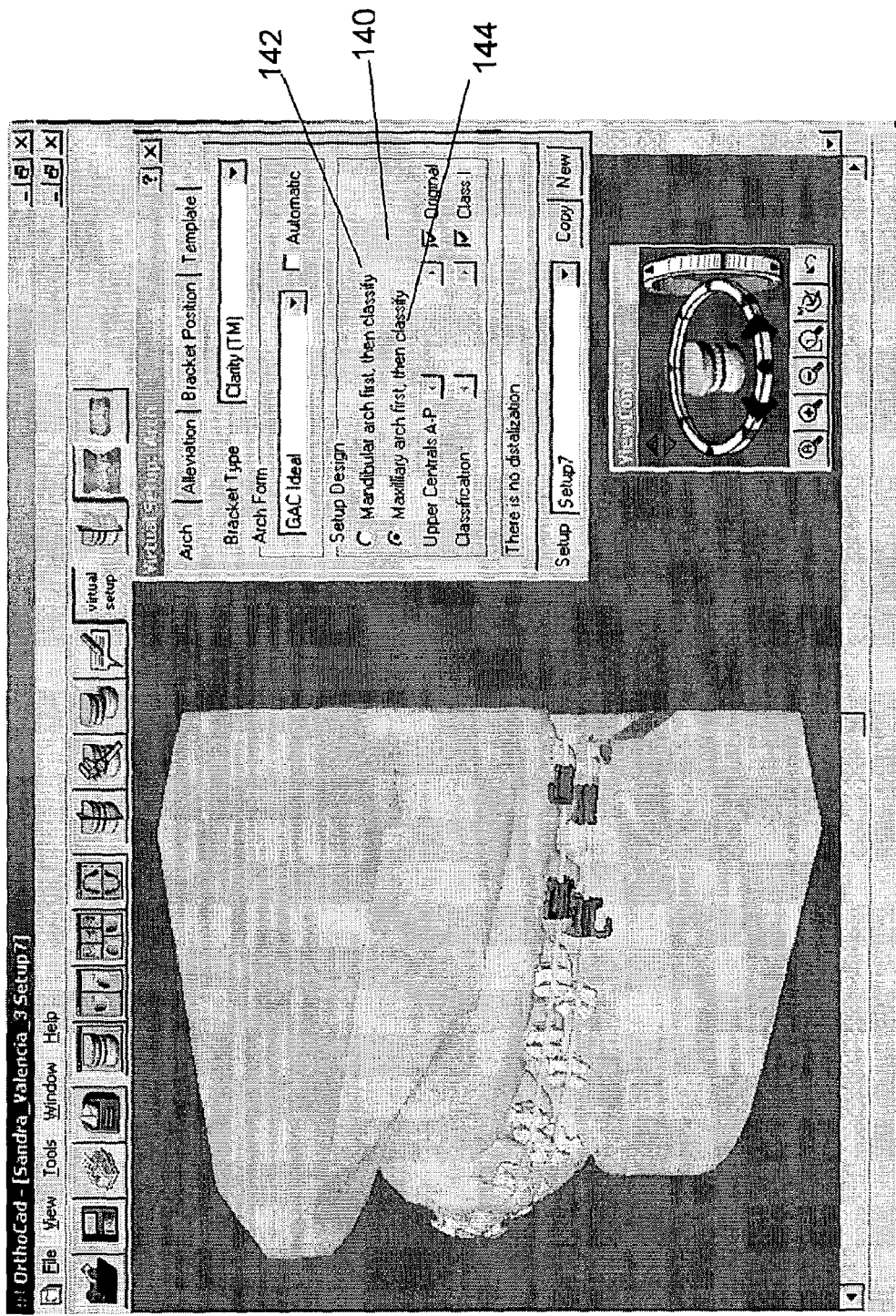
FIG. 8 shows a side view of an outcome of a virtual treatment in which the inter arch relationship is determined according to the fixed maxillary jaw.
Figure 9:
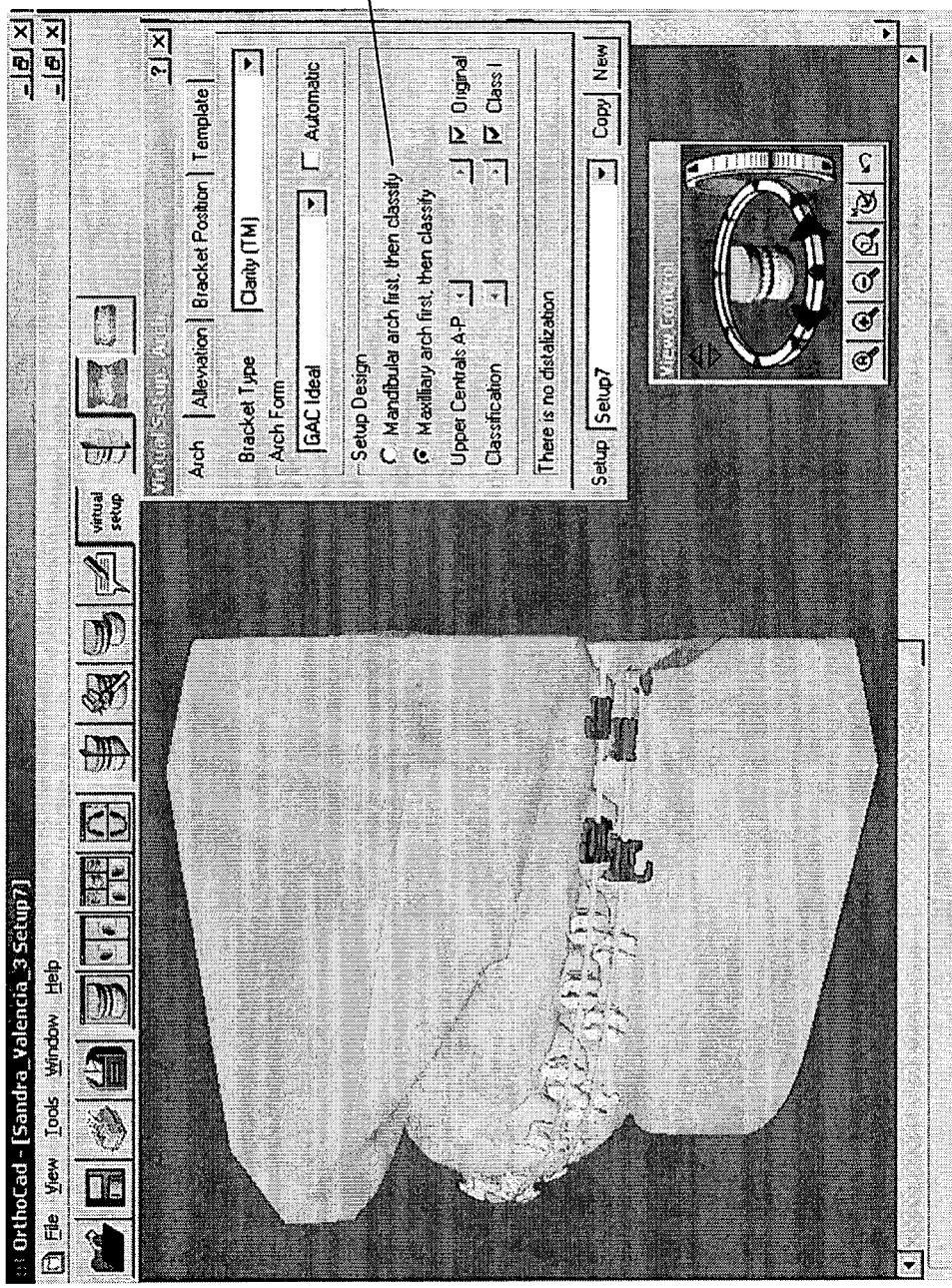
FIG. 9 shows a side view of an outcome of a virtual treatment with the same parameters as in FIG. 8, however, with a fixed mandibular jaw.

The user may also control the parameters of which jaw will be fixed during the procedure. This is achieved by ticking in the set up design user interface 140 between the mandible 142 selection point or the maxilla 144 selection point. In the case of FIG. 8, the parameters of maxillary jaw are fixed during the procedure and after aligning therewith the maxillary arch, the inter arch arrangement is performed. By the default of the system, the mandible parameters are fixed and the maxilla is moved accordingly. The reverse selection is shown in FIG. 9 (145). Thus, as can be seen, in view of the initial structure of the teeth, the two jaws are more forwardly oriented in FIG. 9 as compared to FIG. 8.

Figure 10:
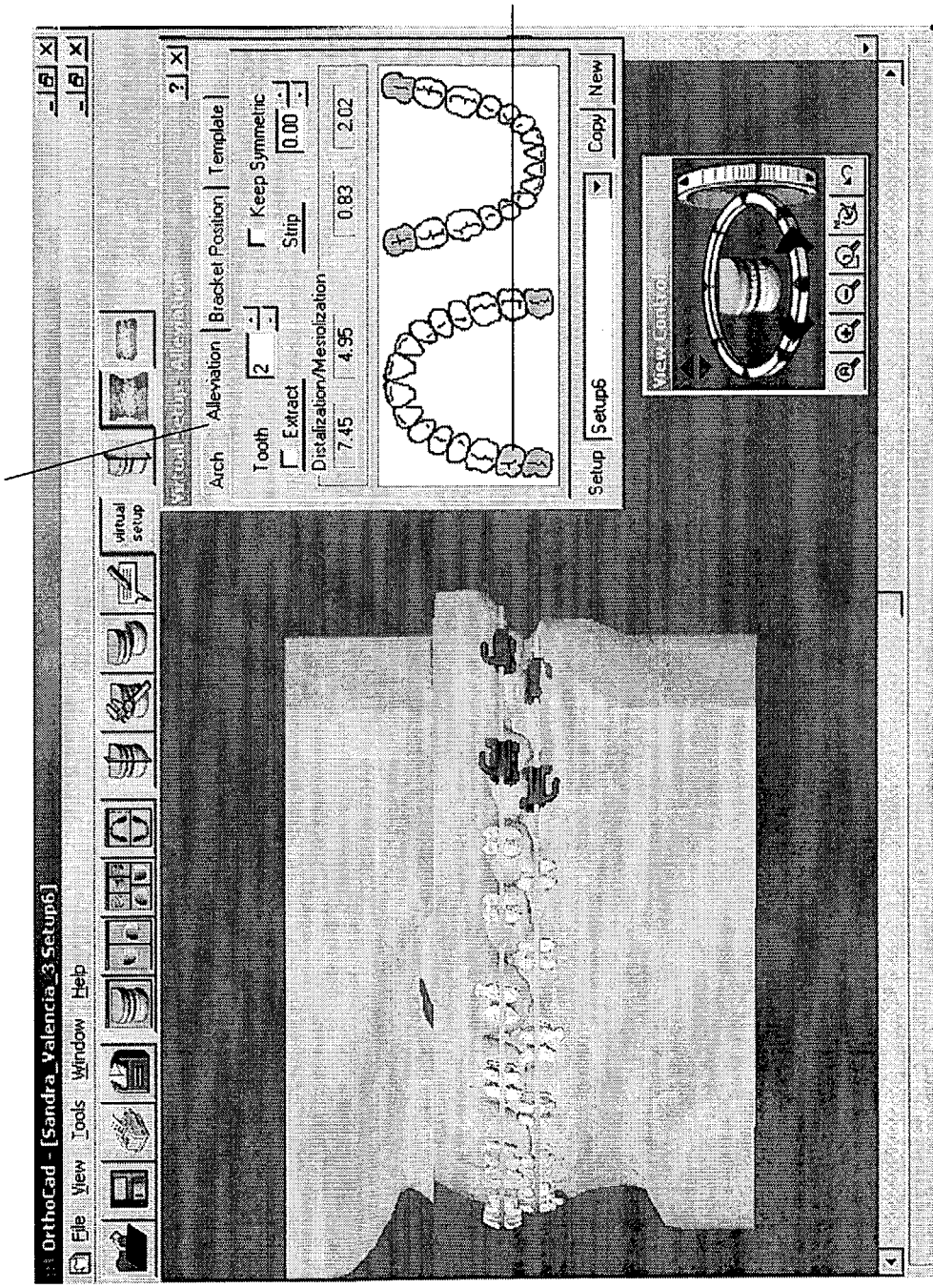
FIG. 10 shows a screen display for selecting a tooth for extraction.
Figure 11:
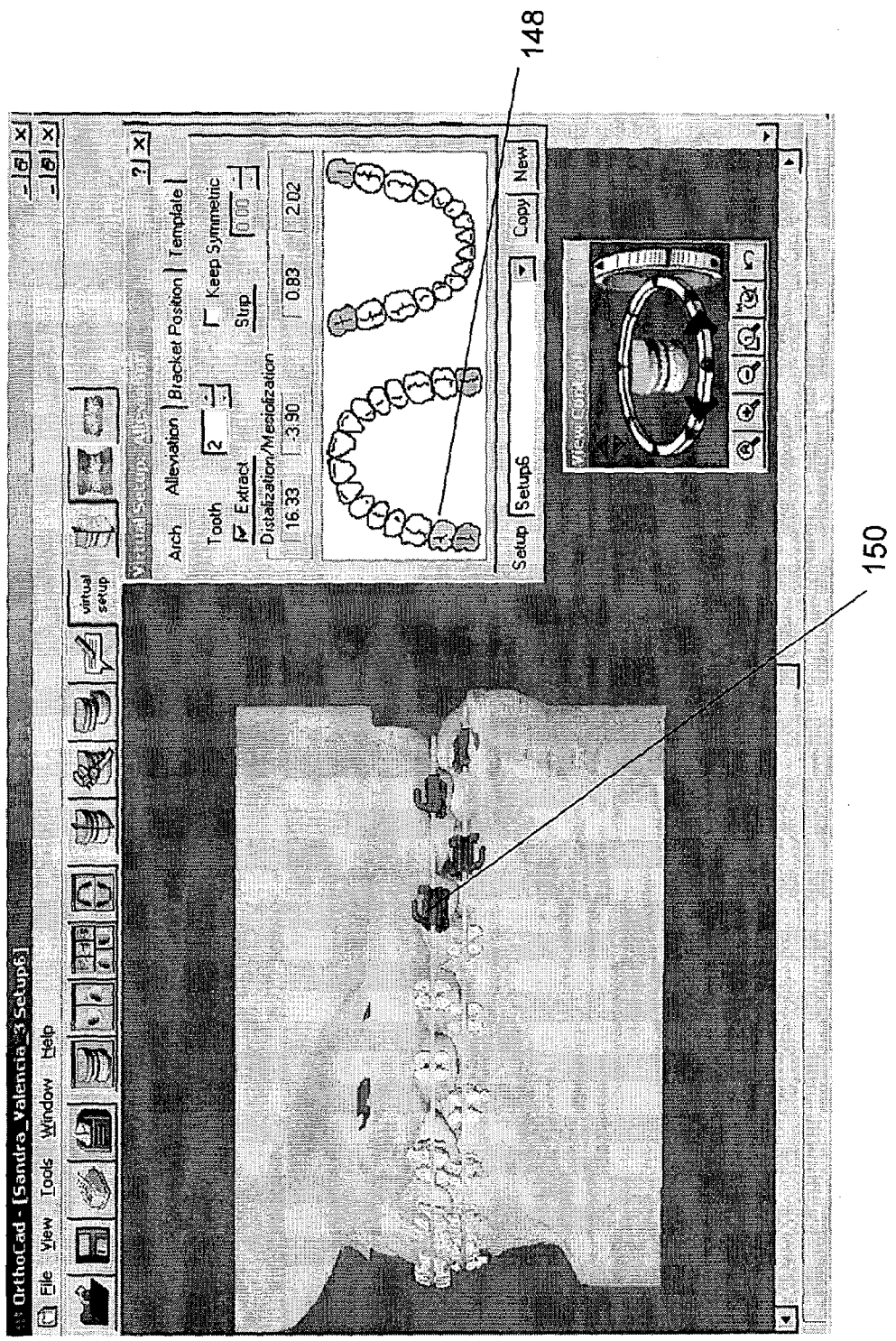
FIG. 11 shows a screen display showing the outcome of a virtual treatment after extracting a tooth.

Another manner of control is a virtual extraction of teeth. In FIG. 10, the treatment is preceded normally without extraction. By ticking Alleviation box 138 and marking in the user interface window 106 the tooth or teeth to be extracted, the marked tooth, in this particular case, the second molar 148 is virtually extracted and the void 150 which is left is at least partially filled by lateral movement of the flanking teeth, as seen in FIG. 11. This feature of the system of the invention enables the user to decide whether extraction of a tooth in a real life treatment will be effective in achieving a desired orthodontic outcome before performing such an irreversible manipulation in the real life treatment.

Figure 2:
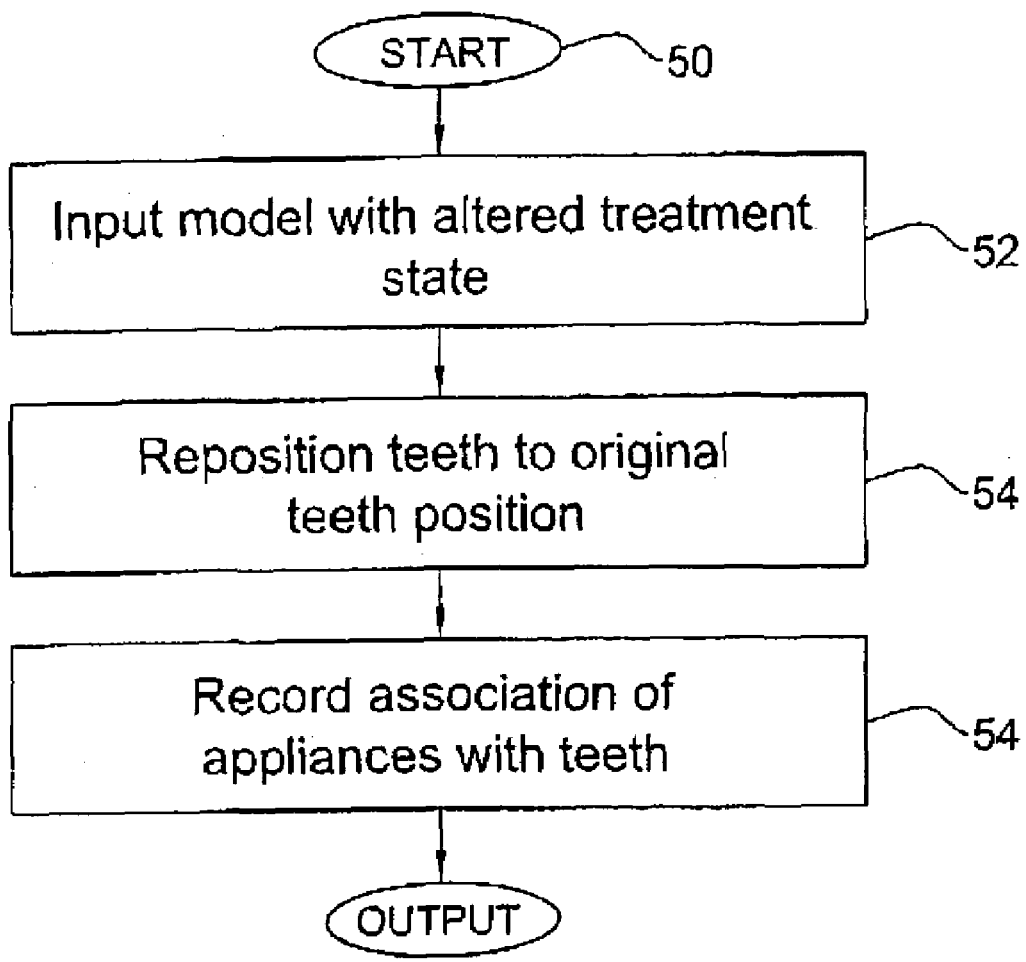
FIG. 2 shows a flow diagram of the manner of utilizing the results of the virtual orthodontic treatment for obtaining data to be used in design of a real-life orthodontic treatment.

Reference is made now to FIG. 2 which shows the manner of using the results of the virtual orthodontic treatment for guidance for the real-life orthodontic treatment. Following start 50, the virtual model with the altered treatment state obtained through the virtual orthodontic treatment (36 in FIG. 1) is inputted at 52. The teeth are then, at 54, permitted to reposition to their original position in the original diagnostic setup model with the orthodontic appliances remaining attached thereon. The association of the orthodontic appliances with the teeth is then recorded as 56 and this is served as an input for guidance of the real-life orthodontic treatment for the purpose of achieving results similar to those obtained in the virtual treatment in accordance with the invention. The manner of association of the orthodontic appliances may be displayed on the screen or may be outputted to a guidance system for proper placing of an orthodontic element on a tooth's surface, such as that described in U.S. Pat. No. 6,334,772.

The invention claimed is:

1. A virtual orthodontic treatment method, comprising:
   (a) providing a virtual diagnostic setup model of teeth of at least one jaw of an individual, associating each teeth in said model with its corresponding virtual orthodontic appliance to obtain a first composite model and repositioning teeth into an initial treatment state according to pre-defined appliances-dependent rules;
   (b) associating a grade with said initial treatment state according to one or more systems for grading an orthodontic model;
   (c) in said initial treatment state, selecting one or more teeth and reassociating teeth with their corresponding virtual orthodontic appliances by changing the position of the appliance corresponding to the selected tooth thereby causing repositioning of the teeth according to the appliance-dependence rules to obtain an altered treatment state,
   (d) associating another grade with said altered treatment state according to said one or more systems for grading an orthodontic model.

2. A method according to claim 1, wherein said reassociating comprising detaching appliance from tooth, changing the position of said appliance on the tooth to effect repositioning of the tooth and reattaching appliance with tooth.

3. A method according to claim 1 wherein said virtual setup model includes teeth of both jaws.

4. A method according to claim 1, wherein the grading is based on measuring one or more of alignment, marginal ridges, buccolingual inclination, overjet, occiusal relationship, occlusal contacts and interproximal contacts.

5. A method according to claim 4, wherein the grading is carried out according to the grading system the American Board of Orthodontics.

6. A method according to claim 1, wherein said orthodontic appliances include brackets that are attached to teeth and a straight arch wire received in a slot of said bracket.

7. A method according to claim 6, wherein the brackets in said first composite model are attached essentially at the center of the crown of the teeth, and said appliances-dependent rules include repositioning of teeth so that the slots of all brackets are aligned in a plane defined by the said arch wire and the teeth are aligned along an arch defined by said arch wire.

8. A method according to claim 7, wherein in the initial treatment stage the one or more brackets are detached from the corresponding teeth, and repositioned in a location on the teeth that is different than in said initial treatment stage.

9. A method according to claim 1, wherein said reassociating is repeated a plurality of times with different positions of brackets and different types of grading after each time, for achieving best grade after said repositioning.

10. A method according to claim 1, wherein a user selects a set of orthodontic appliances for associating with the teeth.

11. A method according to claim 1, comprising automatically selecting a set of orthodontic appliances for associating with the teeth.

12. A method according to claim 1, comprising automatically defining one or more additional orthodontic interventions.

13. A method according to claim 12, wherein said orthodontic interventions are one or both of tooth extraction and tooth stripping.

14. A method according to claim 1, comprising automatically defining one or more additional orthodontic interventions.

15. A method according to claim 12, wherein said additional orthodontic interventions are one or both of tooth extraction and interproximal stripping.

16. A method according to claim 1, wherein a user manually defines one or more additional orthodontic interventions.

17. A method according to claim 12, wherein said additional orthodontic interventions are one or both of tooth extraction and interproximal stripping.

18. A method according to claim 1, wherein the grading system is manually chosen by a user.

19. A method according to claim 1, wherein the grading system is manually chosen by a user from two or more provided grading systems.

20. A method according to claim 1, wherein the grading of the altered treatment state is carried out manually by a user.

21. A method for designing a real life orthodontic treatment, comprising:
(a) providing a virtual diagnostic setup model of an initial state of teeth of at least one jaw of an individual, associating virtual orthodontic appliances with teeth in said model in a first association arrangement to obtain a first composite virtual model;
(b) associating a first grade with said first composite virtual model, according to one or more systems for grading an orthodontic model:
(c) repositioning teeth according to pre-defined appliances-dependent rules, to obtain an initial treatment state with a second association arrangement of said teeth and said appliances;
(d) in said initial treatment state
   selecting one or more teeth and virtually detaching between at least the selected teeth and said orthodontic appliances,
   repositioning said appliances on the teeth and reattaching appliances with teeth thereby altering treatment state and obtaining a second composite virtual model;
   associating a second grade with said second composite model, according to said one or more systems for grading an orthodontic model; and
(e) permitting the teeth to revert back from their state in said second composite virtual model into said initial state with said orthodontic appliance remaining associated with the teeth in a maimer as in said second composite virtual model to obtain a treatment-design virtual model with orthodontic appliances associated with the teeth in a maimer of association to be applied in a real life orthodontic treatment.

22. A method according to claim 21, wherein said virtual setup model includes teeth of both jaws.

23. A method according to claim 21, wherein the grading is based on measuring one or more of alignment, marginal ridges, buccolingual inclination, overjet, ocelusal relationship, occlusal contacts and interproximal contacts.

24. A method according to claim 21, wherein the grading is carried out according to the grading system the American Board of Orthodontics.

25. A method according to claim 21, wherein said orthodontic appliances include brackets that are attached to teeth and an arch wire received in a slot of said bracket.

26. A method according to claim 25, wherein the brackets in said first composite model are attached essentially at the center of the crown of the teeth, and said appliances-dependent rules include repositioning of teeth so that the slots of all brackets become aligned.

27. A method according to claim 26, wherein in the initial treatment stage the appliances are detached from the selected teeth, repositioned and reattached to the teeth, the reattachment of said corresponding brackets being in a location on the teeth that is different than in said initial treatment stage.

28. A method according to claim 21, wherein said repositioning is repeated a plurality of times with different positions of brackets and the resulting improved treatment state is graded after each time, for achieving best grade after said repositioning.

29. A method according to claim 21, wherein a user selects a set of orthodontic appliances for associating with the teeth.

30. A method according to claim 21, comprising automatically selecting a set of orthodontic appliances for associating with the teeth.

31. A method according to claim 21, comprising automatically defining one or more additional orthodontic interventions.

32. A method according to claim 31, wherein said orthodontic interventions are one or both of tooth extraction and tooth stripping.

33. A method according to claim 21, comprising automatically defining one or more additional orthodontic interventions.

34. A method according to claim 33, wherein said additional orthodontic interventions are one or both of tooth extraction and interproximal stripping.

35. A method according to claim 21, wherein a user manually defines one or more additional orthodontic interventions other than association of appliances for the virtual treatment.

36. A method according to claim 35, wherein said additional orthodontic interventions are one or both of tooth extraction and interproximal stripping.

37. A method according to claim 21, wherein the grading system is automatically chosen by a user.

38. A method according to claim 21, wherein the grading system is manually chosen by a user from two or more provided grading systems.

39. A method according to claim 21, wherein the grading of the altered treatment state is carried out manually by a user.

40. A system for virtual orthodontic treatment, comprising:
   (i) a digital interface for receiving digital data representative of a virtual diagnostic setup model of teeth;
   (ii) a processor including a software for
      associating virtual orthodontic appliances with teeth in said model to obtain a first composite model,
      repositioning teeth into an initial treatment state according to pre-defined appliances-dependent rules,
      associating a first grade with said first composite model, according to one or more systems for grading an orthodontic model; and for
      in said initial treatment state, selecting teeth and virtually reassociating said orthodontic appliances with teeth by repositioning appliances on at least selected teeth to obtain an altered treatment state thereby obtaining a second composite virtual model,
      associating a second grade with said second composite model, according to said one or more systems for grading an orthodontic model; and
   (iii) a user interface comprising at least a display for displaying results of the virtual orthodontic treatment.

41. A system according to claim 40, wherein the processor virtually reassociates the orthodontic appliances with the teeth by detaching appliance from teeth, changing the position of appliances on teeth to effect repositioning of the teeth and reattaching appliances with teeth.

42. A system according to claim 40, wherein the grading is based on measuring one or more of alignment, marginal ridges, buccolingual inclination, overjet, occlusal relationship, occlusal contacts and interproximal contacts.

43. A system according to claim 42, wherein the grading is carried out according to the grading system of the American Board of Orthodontics.

44. A system according to claim 40, wherein said orthodontic appliances include brackets that are attached to teeth and an arch wire received in a slot of said bracket.

45. A system according to claim 44, wherein said software initially virtually attaches the brackets essentially at the center of the crown of the teeth, and said appliances-dependent rules include repositioning of teeth so that the slots of all brackets become aligned.

46. A system according to claim 45, in the initial treatment stage said software reassociates one or more teeth with corresponding brackets, such that the position of the brackets is in a location on the teeth that is different than in said initial treatment stage.

47. A system according to claim 40, wherein said reassociating can be repeated a plurality of times with different positions of brackets and the resulting improved treatment state is graded after each time, for achieving best grade after said repositioning.

48. A system according to claim 40, wherein the set of orthodontic appliances is selected by a user.

49. A system according to claim 40, wherein the set of orthodontic appliances is selected automatically by said software.

50. A system according to claim 40, wherein if applicable, said software defines one or more additional orthodontic interventions.

51. A system according to claim 50, wherein said additional orthodontic interventions are one or both of tooth extraction and interproximal stripping.

52. A system according to claim 40, wherein the user interface permits a user to define one or more additional orthodontic interventions.

53. A system according to claim 52, wherein said additional orthodontic interventions are one or both of tooth extraction and interproximal stripping.

54. A system according to claim 40, wherein the software can automatically select the grading system.

55. A system according to claim 40, wherein the user interface permits the user to select a grading system.

56. A system according to claim 40, wherein the user interface permits the user to manually grade the altered treatment state.

57. A system for designing a real life orthodontic treatment, comprising:
   i. a digital interface for inputting a virtual diagnostic setup model of an initial state of teeth of an individual;
   ii. a user interface comprising at least an output for outputting results of virtual orthodontic treatment and information on design of real life orthodontic treatment;
   iii. a processor including a software running thereon for
      associating virtual orthodontic appliances with teeth in said model in a first association arrangement to obtain a first composite virtual model,
      associating a first grade with said first composite model, according to one or more systems for grading an orthodontic model,
      repositioning teeth according to pre-defined appliances-dependent rules, to obtain an initial treatment state with a second association arrangement of said teeth and said appliances,
      in said initial treatment state selecting one or more teeth, virtually reassociating said orthodontic appliances from teeth by repositioning appliances on at least selected teeth to obtain an altered treatment state,
      associating a second grade with said altered treatment state, according to said one or more systems for grading an orthodontic model, thereby obtaining a second composite virtual model,
      permitting the teeth to revert back from their state in said second composite virtual model into said initial state with said orthodontic appliance remaining associated with the teeth in a manner as in said second composite virtual model to obtain treatment-design virtual model with orthodontic appliances associated with the teeth in a manner of association to be applied in a real life orthodontic treatment, and
      outputting data representative of said treatment-design virtual model in a manner suitable for use in the design of the real life orthodontic treatment.

58. A system according to claim 57, wherein the grading is based on measuring one or more of alignment, marginal ridges, buccolingual inclination, overjet, occlusal relationship, ocelusal contacts and interproximal contacts.

59. A system according to claim 58, wherein the grading is carried out according to the grading system of the American Board of Orthodontics.

60. A system according to claim 57, wherein said orthodontic appliances include brackets that are attached to teeth and an arch wire received in a slot of said bracket.

61. A system according to claim 60, wherein said software initially virtually attaches the brackets essentially at the center of the crown of the teeth, and said appliances-dependent rules include repositioning of teeth so that the slots of all brackets become aligned.

62. A system according to claim 61, in the initial treatment stage said software detaches from at least one tooth its corresponding at least one bracket, repositions brackets and reattaches brackets with teeth such that the position of at least one bracket being in a location on the at least one tooth that is different than in said initial treatment stage.

63. A system according to claim 57, wherein said reassociating can be repeated a plurality of times with different positions of brackets and the resulting improved treatment state is graded after each time, for achieving best grade after said repositioning.

64. A system according to claim 57, wherein the set of orthodontic appliances is selected by a user.

65. A system according to claim 57, wherein the set of orthodontic appliances is selected automatically by said software.

66. A system according to claim 57, wherein if applicable, said software defines one or more additional orthodontic interventions.

67. A system according to claim 66, wherein said additional orthodontic interventions are one or both of tooth extraction and interproximal stripping.

68. A system according to claim 57, wherein the user interface permits a user to define one or more additional orthodontic interventions.

69. A system according to claim 68, wherein said additional orthodontic interventions are one or both of tooth extraction and interproximal stripping.

70. A system according to claim 57, wherein the software can automatically select the grading system.

71. A system according to claim 57, wherein the user interface permits the user to select a grading system.

72. A system according to claim 57, wherein the user interface permits the user to manually grade the altered treatment state.

73. A method according to claim 1, wherein step (c) is performed such as to yield a better grade in step (d) than in step (b).

74. A method according to claim 21, wherein said second grade is a better grade than said first grade, according to said one or more systems for grading an orthodontic model.

75. A system according to claim 40, wherein said processor includes a software for obtaining a second virtual model, such that said second grade is better than said first grade.

76. A system according to claim 57, wherein said second grade is a better grade than said first grade, according to said one or more systems for grading an orthodontic model.

77. A virtual orthodontic treatment method, comprising:

(a) providing a virtual diagnostic setup model of teeth of at least one jaw of an individual, associating each teeth in said model with its corresponding virtual orthodontic appliance to obtain a first composite model and repositioning teeth into an initial treatment state according to pre-defined appliances-dependent rules;

(b) applying one or more systems for grading an orthodontic model to said initial treatment state and obtaining a grade associated with said initial treatment state;

(c) in said initial treatment state, selecting one or more teeth and reassociating teeth with their corresponding virtual orthodontic appliances by changing the position of the appliance corresponding to the selected tooth thereby causing repositioning of the teeth according to the appliance-dependence rules to obtain an altered treatment state;

(d) applying said one or more systems for grading an orthodontic model to said altered treatment state and obtaining another grade associated with said altered treatment state.

78. A method according to claim 77, wherein step (c) is performed such as to yield a better grade in step (d) than in step (b).

* * * * *

UNITED STATES PATENT AND TRADEMARK OFFICE
CERTIFICATE OF CORRECTION

PATENT NO.       : 7,074,039 B2                                              Page 1 of 1
APPLICATION NO.  : 10/426975
DATED            : July 11, 2006
INVENTOR(S)      : Kopelman It is certified that error appears in the above-identified patent and that said Letters Patent is hereby corrected as shown below:

Claim 1, Column 14, Line 4,
Please delete
"maimer" and replace with -- manner --

Signed and Sealed this

Thirtieth Day of January, 2007

JON W. DUDAS
*Director of the United States Patent and Trademark Office*